US012773541B2

(12) United States Patent
Brahmandam et al.

(10) Patent No.: US 12,773,541 B2
(45) Date of Patent: Oct. 27, 2026

(54) SYSTEMS AND METHODS FOR BI-DIRECTIONAL ENDOVASCULAR ACCESS FOR DIAGNOSTIC AND THERAPEUTIC INTERVENTIONS

(71) Applicant: YALE UNIVERSITY, New Haven, CT (US)

(72) Inventors: Anand Brahmandam, New Haven, CT (US); Abhay Ramachandra, New Haven, CT (US); Alan Dardik, Bethany, CT (US)

(73) Assignee: Yale University, New Haven, CT (US)

( * ) Notice: Subject to any disclaimer, the term of this patent is extended or adjusted under 35 U.S.C. 154(b) by 1250 days.

(21) Appl. No.: 17/314,653

(22) Filed: May 7, 2021

(65) Prior Publication Data

US 2021/0346659 A1 Nov. 11, 2021

Related U.S. Application Data

(60) Provisional application No. 63/022,138, filed on May 8, 2020.

(51) Int. Cl.
*A61M 29/02* (2006.01)
*A61M 25/10* (2013.01)
*A61M 39/22* (2006.01)

(52) U.S. Cl.
CPC ............ *A61M 29/02* (2013.01); *A61M 25/10* (2013.01); *A61M 39/223* (2013.01); *A61M 2025/1052* (2013.01); *A61M 2025/1081* (2013.01); *A61M 2039/229* (2013.01)

(58) Field of Classification Search
CPC .......... A61M 25/10; A61M 2025/1052; A61M 2025/1081; A61M 39/223; A61M 2039/229; A61M 29/02; A61F 2/82; A61F 2/856; A61F 2/962; A61F 2002/826
See application file for complete search history.

(56) References Cited

U.S. PATENT DOCUMENTS 5,092,846 A * 3/1992 Nishijima ......... A61M 39/0606 604/167.04
5,755,735 A * 5/1998 Richter ..................... A61F 2/07 128/898
6,086,557 A * 7/2000 Morejohn ........... A61M 1/3659 604/509
2002/0169377 A1* 11/2002 Khairkhahan . A61B 17/320725 600/433
2003/0097169 A1* 5/2003 Brucker ................ A61F 2/9662 623/1.11
2005/0283179 A1* 12/2005 Lentz ................ A61M 25/0054 264/145
2007/0038245 A1* 2/2007 Morris ............... A61B 17/0218 606/213
2010/0312261 A1* 12/2010 Suzuki ................ A61J 15/0023 606/153
2012/0010563 A1* 1/2012 Ravikumar ....... A61M 25/0662 604/171

* cited by examiner

*Primary Examiner* — Michael J Tsai
*Assistant Examiner* — Justin L Zamory
(74) *Attorney, Agent, or Firm* — Riverside Law LLP

(57) ABSTRACT

The present invention relates to a sheath system that enables endovascular imaging and treatment of concomitant multiple lesions, both in antegrade and retrograde direction in a blood vessel. Further, the present invention relates to a method for using the sheath system enabling endovascular imaging and treatment of concomitant multiple lesions, both in antegrade and retrograde direction.

18 Claims, 16 Drawing Sheets

SYSTEMS AND METHODS FOR BI-DIRECTIONAL ENDOVASCULAR ACCESS FOR DIAGNOSTIC AND THERAPEUTIC INTERVENTIONS

CROSS REFERENCE TO RELATED APPLICATIONS

This application claims priority to U.S. Provisional Application No. 63/022,138, filed May 8, 2020, the contents of which are incorporated by reference herein in its entirety.

BACKGROUND OF THE INVENTION

Currently, vascular access for endovascular interventions is obtained via a single lumen, unidirectional sheath that facilitates access for endovascular imaging and interventions upstream or antegrade to the access site. However, sheaths permitting bi-directional access, both upstream and downstream to the puncture site, are not known. Most often, bi-directional access would require a separate access site on the blood vessel, artery or vein, and, or a separate procedure to facilitate vascular access. Multiple interventions and multiple vascular access sites increase the risk of complications related from the access. Moreover, the existing devices fail to provide simultaneous bi-directional endovascular access for imaging and interventions.

Thus, there is a need in the art for a single device, or sheath, to provide bi-directional functionality. The present invention meets this need.

SUMMARY OF THE INVENTION

In one aspect, the present invention relates to a bi-directional sheath system comprising: a sheath body having an elongated cylindrical body and defining an interior lumen in communication with a first opening at the proximal end and second opening at the distal end and a third opening located between the first opening and the second opening of the sheath body; wherein the sheath body comprises at least one dilator, selected from the group consisting of an antegrade dilator and a retrograde dilator, wherein the antegrade dilator comprises a lumen connecting the first opening to second opening, and the retrograde dilator comprises a lumen connecting the second opening to the third opening. In one embodiment, the distance between the first opening and the third opening is less than the distance between the second opening and the third opening. In one embodiment, the antegrade dilator and the retrograde dilator are removable. In one embodiment, the retrograde dilator comprises at least one preformed curve at proximal end, wherein the at least one preformed curve is at least partially flexible. In one embodiment, the sheath body further comprises a side lumen fluidly connected to the sheath body through the third opening. In one embodiment, the side lumen has an angle ranging between 25°-75° with respect to the sheath body. In one embodiment, the sheath body further comprises a side port at the distal end, wherein the side port is in fluid communication with the sheath body. In one embodiment, the side port is further connected to a side port lumen with a three-way stopcock, wherein the side port lumen and the three-way stopcock allow for controlled release of fluids selected from the group consisting of saline and medicine into the sheath body. In one embodiment, the sheath body further comprises an intraluminal balloon assembly in fluid connection with an inflation port located near the distal end through an inflation lumen located therebetween, wherein the luminal balloon assembly can be inflated through the inflation lumen and the inflation port to occlude proximal end of sheath body, thereby providing fixture of the antegrade dilator in place. In on embodiment, the sheath body further comprises an intraluminal trapdoor and a deployment assembly, wherein the intraluminal trapdoor is hingedly secured to sheath body and extend radially within sheath lumen to block access to first opening when deployed. In one embodiment, the deployment assembly is configured to actuate a crevice to move laterally, thereby releasing the intraluminal trapdoor into a retracted position, allowing access through the first opening.

In another aspect, the present invention relates to a method of using a bidirectional sheath system comprising: providing a bi-directional sheath system having a sheath body having an elongated cylindrical body and defining an interior lumen in communication with a first opening at a proximal end, a second opening at a distal end and a third opening between the first opening and the second opening; wherein the sheath body comprises at least one dilator, selected from the group consisting of an antegrade dilator and a retrograde dilator; inserting the at least one dilator into the sheath interior lumen; introducing sheath body through a guide wire to a blood vessel access site; removing the at least one dilator through the guidewire to release their respective configuration within the blood vessel. In one embodiment, the distance between the first opening and the third opening is less than the distance between the second opening and the third opening. In one embodiment, the retrograde dilator comprises at least one preformed curve (curved region) at proximal end, wherein the curved region is at least partially flexible, such that the curved region may be temporarily straightened using a stylet. In one embodiment, sheath body further comprises a side lumen fluidly connected to sheath body through the third opening. In one embodiment, the side lumen has an angle ranging between 25°-75° with respect to the sheath body. In one embodiment, the sheath body further comprises a side port at the distal end, wherein the side port is in fluid communication with the sheath body. In one embodiment, the side port is further connected to a side port lumen with a three-way stopcock, wherein the side port lumen and the three-way stopcock allow for controlled release of fluids selected from the group consisting of saline and medicine into the sheath body. In one embodiment, the sheath body further comprises an intraluminal balloon assembly in fluid connection with an inflation port located near the distal end through an inflation lumen located therebetween, wherein the luminal balloon assembly can be inflated through the inflation lumen and the inflation port to occlude proximal end of sheath body, thereby providing fixture of the antegrade dilator in place. In one embodiment, the sheath body further comprises an intraluminal trapdoor, a crevice and a deployment assembly, wherein the intraluminal trapdoor is hingedly secured to sheath body and extends radially within the sheath lumen to block access to first opening when deployed. In one embodiment, the deployment assembly is configured to actuate the crevice to move laterally, thereby releasing the intraluminal trapdoor into a retracted position, allowing access through the first opening.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 1 comprising FIG. 1A through FIG. 1D depicts a side view of an exemplary bi-directional sheath system that enables endovascular imaging and treatment of concomitant multiple lesions, both antegrade and retrograde to the vascular access site.

FIG. 2 comprising FIG. 2A through FIG. 2C depicts an exemplary bi-directional sheath system that enables endovascular imaging and treatment of concomitant multiple lesions, both antegrade and retrograde to the vascular access site.

FIG. 3 comprising FIG. 3A through FIG. 3D depicts an exemplary bi-directional sheath system that enables endovascular imaging and treatment of concomitant multiple lesions, both antegrade and retrograde to the vascular access site.

FIG. 4 comprising FIG. 4A through FIG. 4D depicts an exemplary bi-directional sheath system that enables endovascular imaging and treatment of concomitant multiple lesions, both antegrade and retrograde to the vascular access site.

DETAILED DESCRIPTION

Figure 1A:
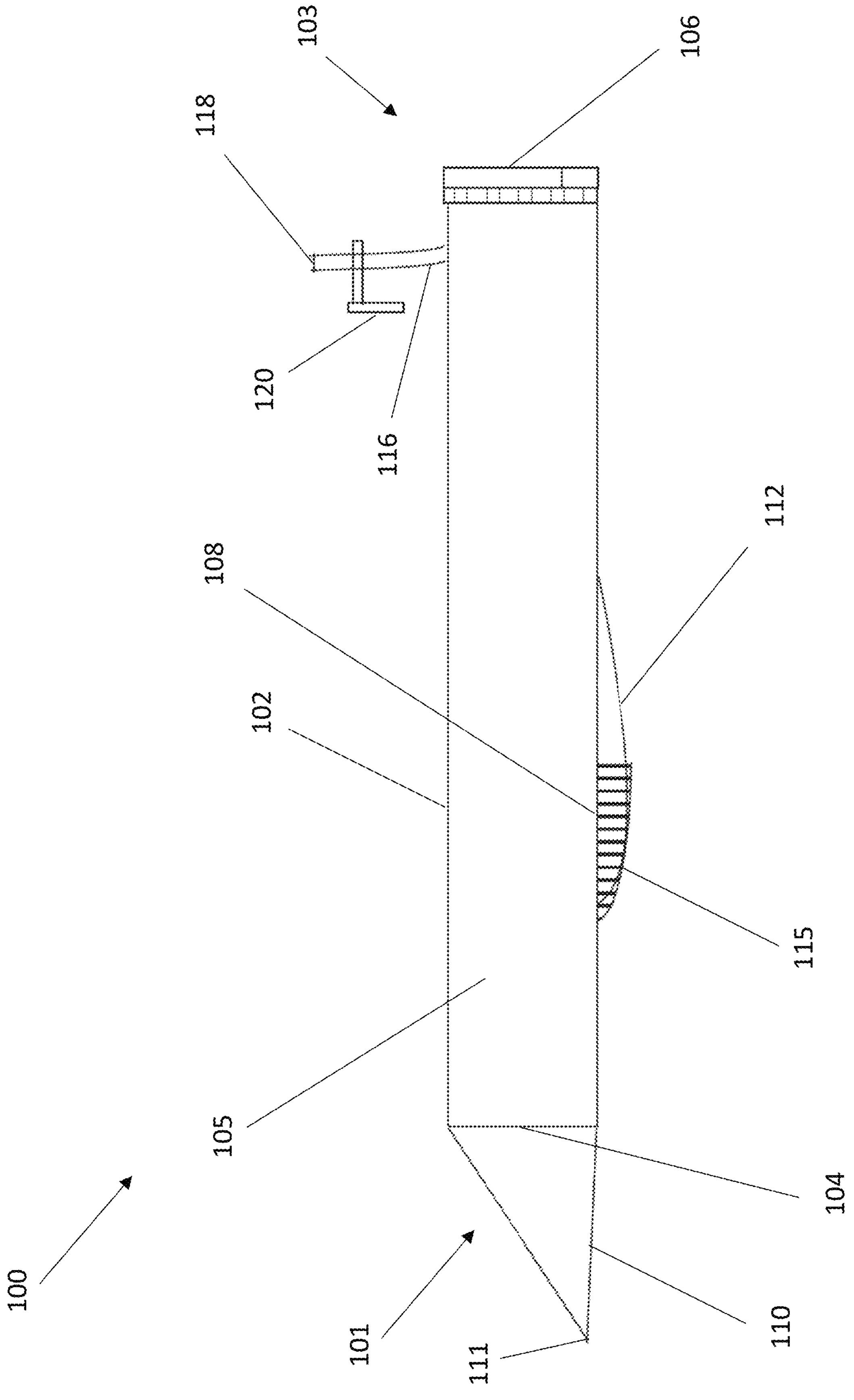
FIG. 1A depicts a side view of an exemplary bi-directional sheath system.

It is to be understood that the figures and descriptions of the present invention have been simplified to illustrate elements that are relevant for a clear understanding of the present invention, while eliminating, for the purpose of clarity, many other elements found in the field of diagnostic and therapeutic devices, including those indicated for the vascular access for endovascular interventions. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, exemplary materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The terms "patient," "subject," "individual," and the like are used interchangeably herein, and refer to any animal amenable to the systems, devices, and methods described herein. The patient, subject or individual may be a mammal, and in some instances, a human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Bi-Directional Sheath System

The present invention relates in part to a bi-directional sheath system that provides bi-directional vascular access. This invention allows for vascular access both upstream and downstream from a single access point. In one embodiment, bi-directional sheath system enables endovascular imaging and treatment of concomitant multiple lesions, both antegrade and retrograde to the vascular access site. In one embodiment, the bi-directional sheath system may be introduced into the blood vessel, artery or vein. Further, the devices, systems and methods described herein have the potential to transform modes of endovascular imaging and treatment of blood vessels, relating to the fields of cardiology, radiology, cardiothoracic surgery, pulmonology, nephrology and vascular surgery. Further, the devices, systems and methods described herein may reduce the number of procedures performed for endovascular imaging and treatment of multiple concomitant lesions in blood vessels. In one embodiment, this invention may reduce the number of blood vessel access sites for endovascular imaging and treatment of multiple concomitant lesions, thus dramatically reducing the rate of complications from access.

Referring now to FIG. 1A, an exemplary bi-directional sheath system 100 of the present invention is shown. Bi-directional sheath system 100 comprises a proximal end 101, a distal end 103 and a sheath body 102 therebetween. Sheath body 102 has an elongated cylindrical body comprising a sheath lumen 105 with a diameter ranging between about 5-9 French. In one embodiment, sheath lumen 105 may have a diameter less than 5 French. In one embodiment, sheath lumen 105 may have a diameter larger than 9 French. In one embodiment, sheath body 102 is ranging approximately between 5 cm-20 cm in length, however any suitable length may be used. Sheath body 102 comprises a first opening 104 at proximal end 101, a second opening 106 at distal end 103 and a third opening 108. In one embodiment, third opening 108 is located between first opening 104 and second opening 106 at any suitable distance away from first opening 104 and second opening 106. In one embodiment, the distance between first opening 104 and third opening 108 is more than the distance between the second opening 106 and the third opening 108. In one embodiment, the distance between first opening 104 and third opening 108 is less than the distance between the second opening 106 and the third opening 108. In one embodiment, first opening 104 and second opening 106 have a diameter ranging between 1.9 mm-3.3 mm. In one embodiment, third opening 108 has a diameter ranging between 1.9 mm-3.3 mm. In one embodiment, first opening 104, second opening 106 and third opening 108 may have a diameter less than 1.9 mm. In one embodiment, first opening 104, second opening 106 and third opening 108 may have a diameter larger than 3.3 mm. First opening 104 and third opening 108 may include radiopaque markers to aid a user in the placement and positioning of sheath body 102.

Second opening 106 provides access to the sheath lumen 105 for introduction of catheters, balloons and stent technology to complete the intended imaging or treatment.

Sheath body 102 further comprises a side lumen 115. Side lumen 115 is fluidly connected to sheath body 102 through third opening 108. In one embodiment, side lumen 115 is a compliant and flexible component. In one embodiment, side lumen 115 has an angle ranging between about 25°-75° with respect to sheath body 102. In one embodiment, side lumen 115 may be positioned anywhere about a perimeter of sheath body 102.

In one embodiment, sheath body 102 may be constructed from a flexible polymer material or kink-resistant metal braid including but not limited to stainless steel or cobalt chromium. In one embodiment, sheath body may be made from a polymeric material, such as silicone, nylon, or urethane. Any medically acceptable thermoplastic or thermoset material may be used, including PTFE, a fluoropolymer, polyethylene, polypropylene, acetal, urethane, and others, however, it may be constructed from any material suitable for use within a blood vessel. In one embodiment, sheath body 102 may be made from a flexible material so that it is compliant and maneuverable throughout the length of sheath body 102 and at least at first opening 104, second opening 106 and third opening 108.

Figure 1B:
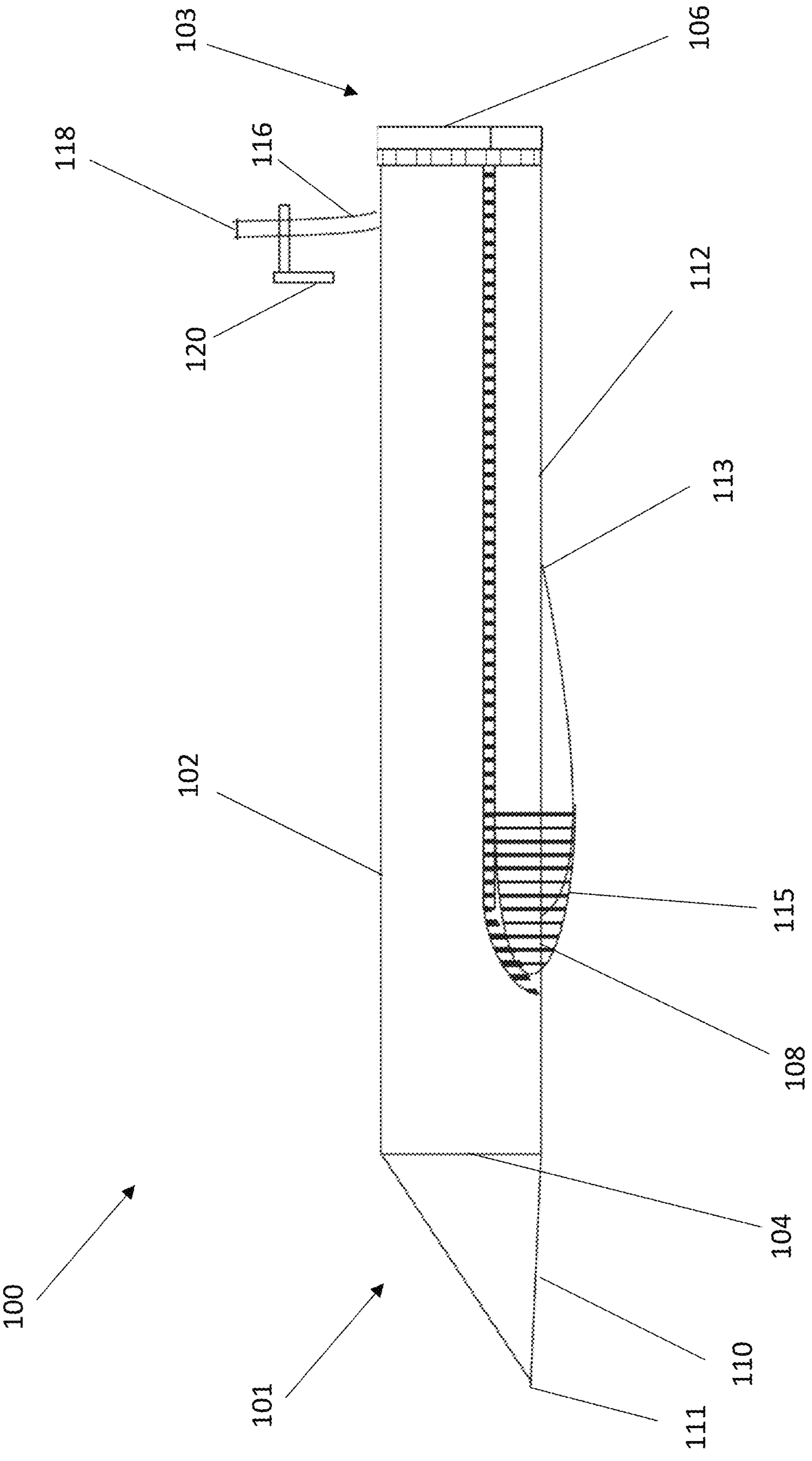
FIG. 1B depicts a side view detailing the common lumen and dual-dilator system of an exemplary bi-directional sheath system.

Sheath body 102 comprises an antegrade dilator 110 and a retrograde dilator 112 (shown in FIG. 1B). This two-pronged dilator system (comprising antegrade dilator 110 and a retrograde dilator 112) is intended for providing support and rigidity to the sheath system during introduction into the blood vessel. Antegrade dilator 110 and retrograde dilator 112 are positioned in place through sheath lumen 105. In one embodiment, antegrade dilator 110 and retrograde dilator 112 are removable. Antegrade dilator 110 comprises a lumen connecting first opening 104 to second opening 106. In one embodiment, the lumen may be used for guide wire access. In one embodiment, antegrade dilator 110 has a diameter ranging from 5-9 French at first opening 104. In one embodiment, antegrade dilator 110 has a diameter ranging from approximately 1.2 mm-3 mm at second opening 106. In one embodiment, antegrade dilator 110 is tapered at proximal end 101 for easier insertion. Antegrade dilator 110 further comprises an opening 111 at the end of proximal end 101. In one embodiment, the diameter of opening 111 ranges from 0.5 mm-1.2 mm. In one embodiment, first opening 104 is constructed so that it becomes occluded when antegrade dilator 110 is placed into the sheath and through first opening 104. In one embodiment, second opening 106 is of a bi-luminal construction such that it includes a antegrade dilator 110 and retrograde dilator 112. In one embodiment, antegrade dilator 110 and retrograde dilator 112 have the same diameter at second opening 106. In one embodiment, antegrade dilator 110 has a diameter larger than retrograde dilator 112 at second opening 106. In one embodiment, antegrade dilator 110 has a diameter smaller than retrograde dilator 112 at second opening 106. In one embodiment, antegrade dilator 110 is oriented towards the heart/head.

Antegrade dilator 110 shares sheath lumen 105 with retrograde dilator 112 from second opening 106 to third opening 108. From third opening 108 toward first opening 104, antegrade dilator 110 has a larger diameter to fit sheath lumen 105 and occlude first opening 104.

In one embodiment, antegrade dilator 110 may further include a radiopaque marker, which in one example is a circular marker band disposed around the tip of antegrade dilator 110. The marker band can include platinum, tantalum, palladium, gold, or any similar dense metal element, alloy, or compound that is visualized by imaging techniques.

Figure 1C:
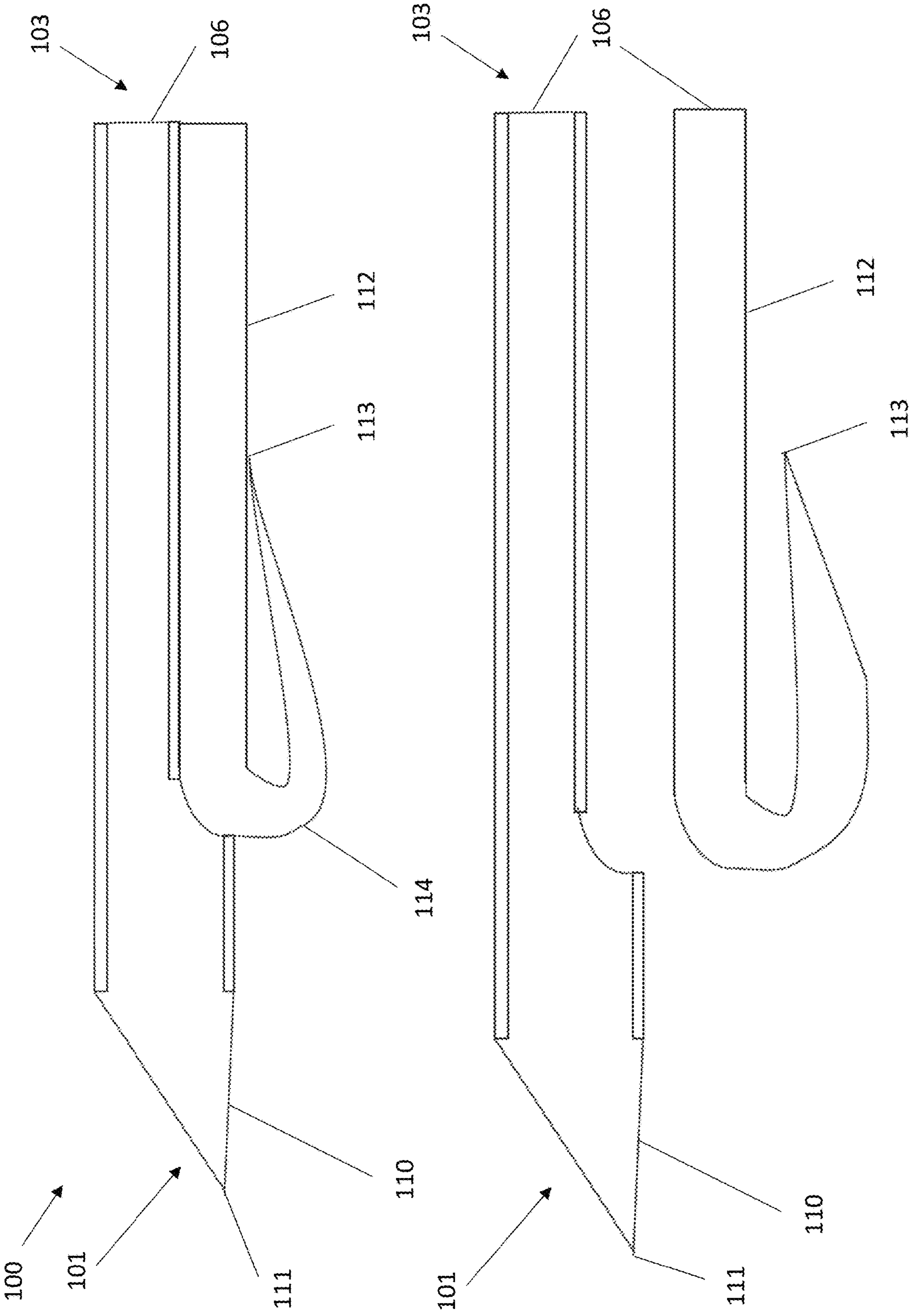
FIG. 1C depicts a side view of the dilators used to introduce an exemplary bi-directional sheath system.

Retrograde dilator 112 connects second opening 106 to third opening 108. Retrograde dilator 112 comprises a lumen for guide wire access. In one embodiment, retrograde dilator 112 has a diameter ranging from approximately 1 mm-2 mm. In some embodiments, as shown in FIG. 1C, retrograde dilator 112 comprises at least one preformed curve (curved region) 114. Curved region 114 can have any curved configuration, including but not limited to loops, bends, hooks, spirals, twists, pigtail curves, Judkins style curves, Amplatz style curves, SOS style curves, cobra style curves, Simmons style curves, Bernstein style curves, and the like in a primary curve, secondary curve, tertiary curve, or more. Curved region 114 may be pre-formed, such as by heat setting. In one embodiment, retrograde dilator 112 may include portions or regions having the desired stiffness, rigidity, and flexibility necessary for proper insertion into the subject and subsequent functionality. In some embodiments, curved region 114 is at least partially flexible, such that curved region 114 may be temporarily straightened using a stylet, or such that the at least one preformed curve may be advanced over a guidewire. In some embodiments, curved region 114 ensures that side lumen 115 stays connected to sheath body 102, so to prevent damage to the wall of the intended blood vessel during introduction of sheath body 102 (FIG. 1B). Retrograde dilator 112 further comprises an opening 113 at distal end 103. In one embodiment, the diameter of opening 113 ranges from 0.5 mm-1.2 mm. In one embodiment, retrograde dilator 112 is oriented towards the feet, if antegrade dilator 110 is oriented towards the head. In one embodiment, retrograde dilator 112 is oriented towards the head, if antegrade dilator 110 is oriented towards the feet.

In one embodiment, antegrade dilator 110 and retrograde dilator 112 are each made of a flexible polymer. Some examples of suitable polymers may include, but are not limited to, polytetrafluoroethylene (PTFE), ethylene tetrafluoroethylene (ETFE), fluorinated ethylene propylene (FEP), polyoxymethylene (POM, for example, DELRIN® available from DuPont), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plasties), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In one embodiment, antegrade dilator 110 and retrograde dilator 112 may be made of soft polymer material to facilitate movement through the patient's blood vessels. The soft polymer is less rigid and more malleable than the hard polymer and less likely to bounce or move suddenly when contacts the vessel wall.

Sheath body 102 may further comprise a side port 116 at distal end 103. Side port 116 is in fluid communication with sheath body 102. Side port 116 may be further connected to side port lumen 118 with three-way stopcock 120. Side port lumen 118 with three-way stopcock 120 allows for controlled release of fluids (e.g., saline, medicine, etc.) into sheath body 102.

Figure 1D:
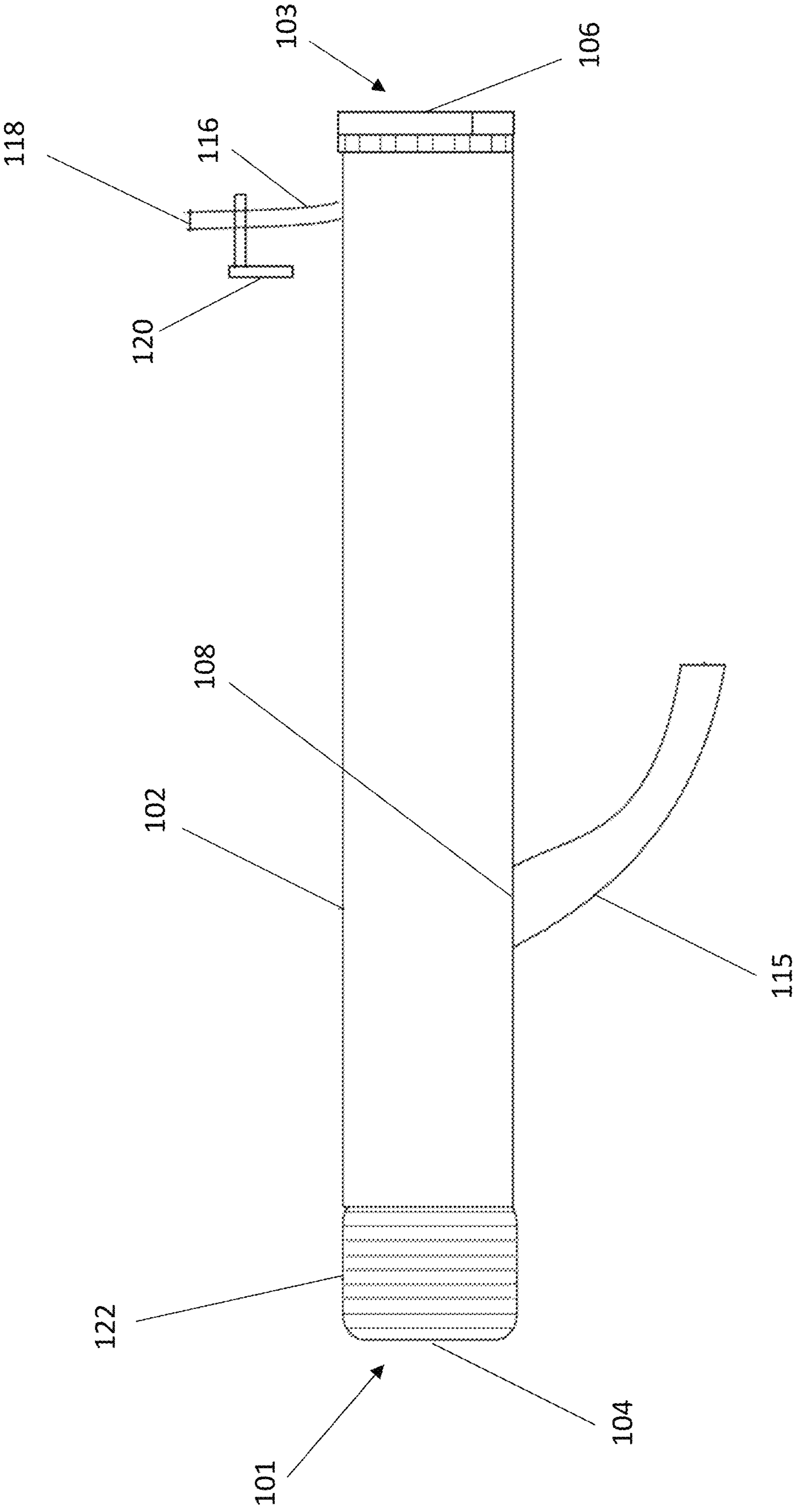
FIG. 1D depicts a side view configuration of an exemplary bi-directional sheath system, after removal of the dilators.

Referring now to FIG. 1D, a side-view of the bi-directional sheath body 102 is shown in the intended intravascular configuration, without antegrade dilator 110 and retrograde dilator 112 in place. Sheath body 102 further comprises an end unit 122 connected to sheath body 102 at proximal end 101. In one embodiment, end unit 122 has a length approximately ranging between 1 cm-5 cm. In one embodiment, end unit 122 may have a length less than 1 cm. In one embodiment, end unit 122 may have a length more than 5 cm. In one embodiment, end unit 122 is flexible and compliant. In one embodiment, end unit 122 has the same diameter as sheath body 102. In one embodiment, end unit 122 is constructed from material including but not limited to Polyether block Amide (PEBA), Polytetrafluoroethylene (PTFE), stainless steel, Polyoxymethylene (POM), Polyvinyl chloride (PVC), Marlex and Nylon to allow end unit 122 to be flexible and can have angles ranging between 110-170 degrees to sheath body 102. This configuration permits introduction of guidewire, balloon and stent devices in a bi-directional orientation.

Figure 2A:
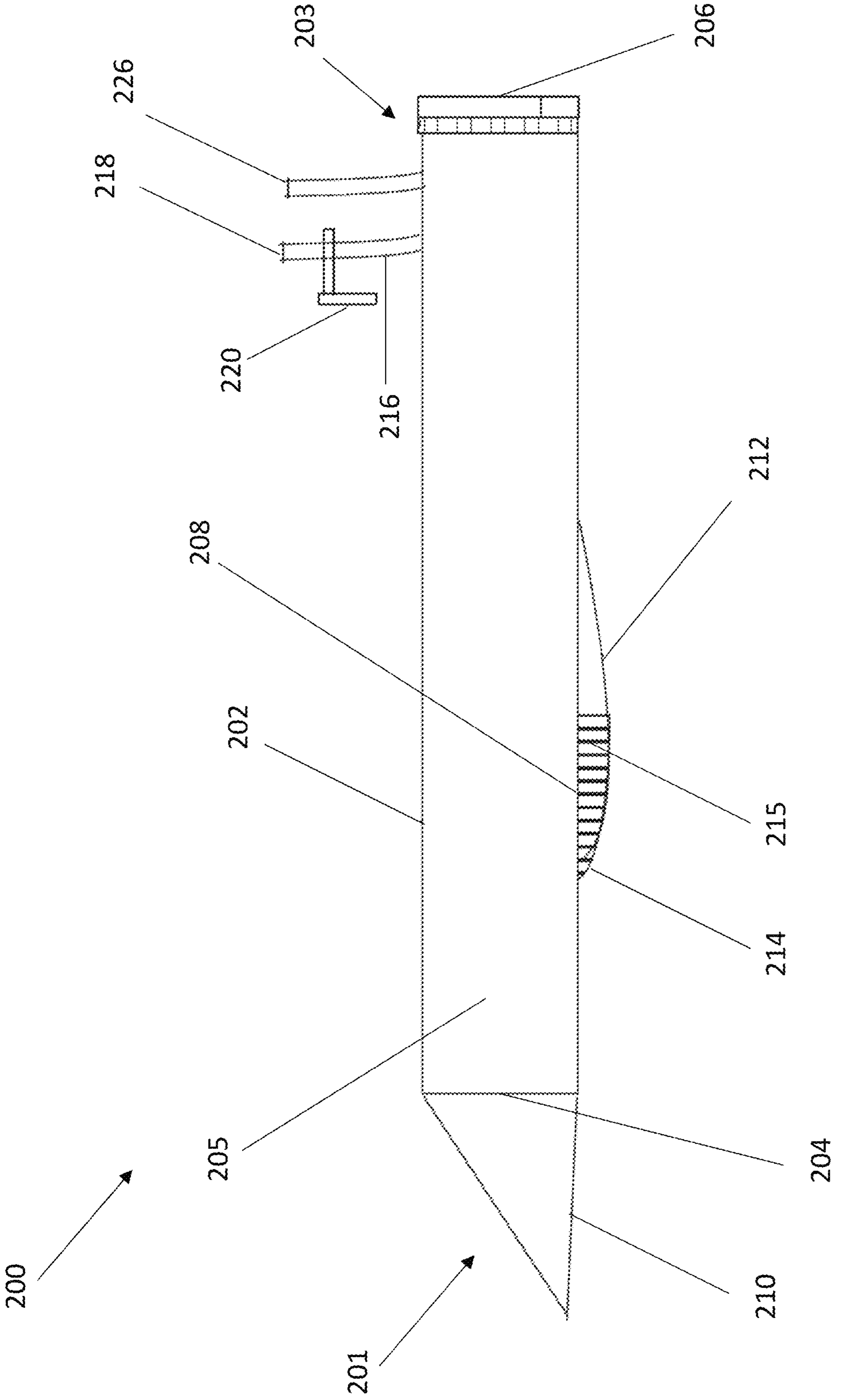
FIG. 2A depicts a side view of an exemplary bi-directional sheath system.
Figure 2B:
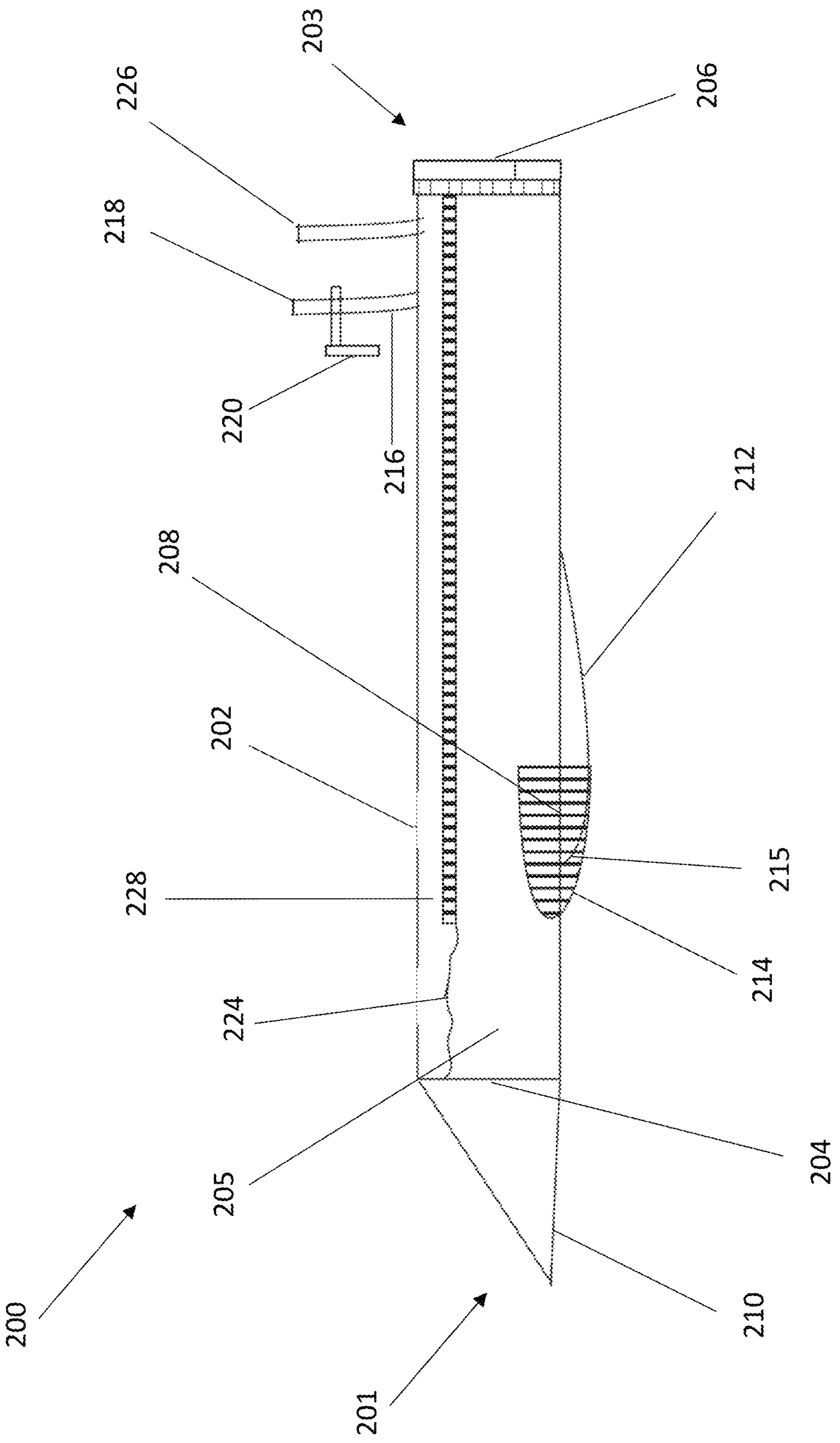
FIG. 2B depicts a side view detailing the common lumen, balloon and dual-dilator assembly of an exemplary bi-directional sheath system.
Figure 2C:
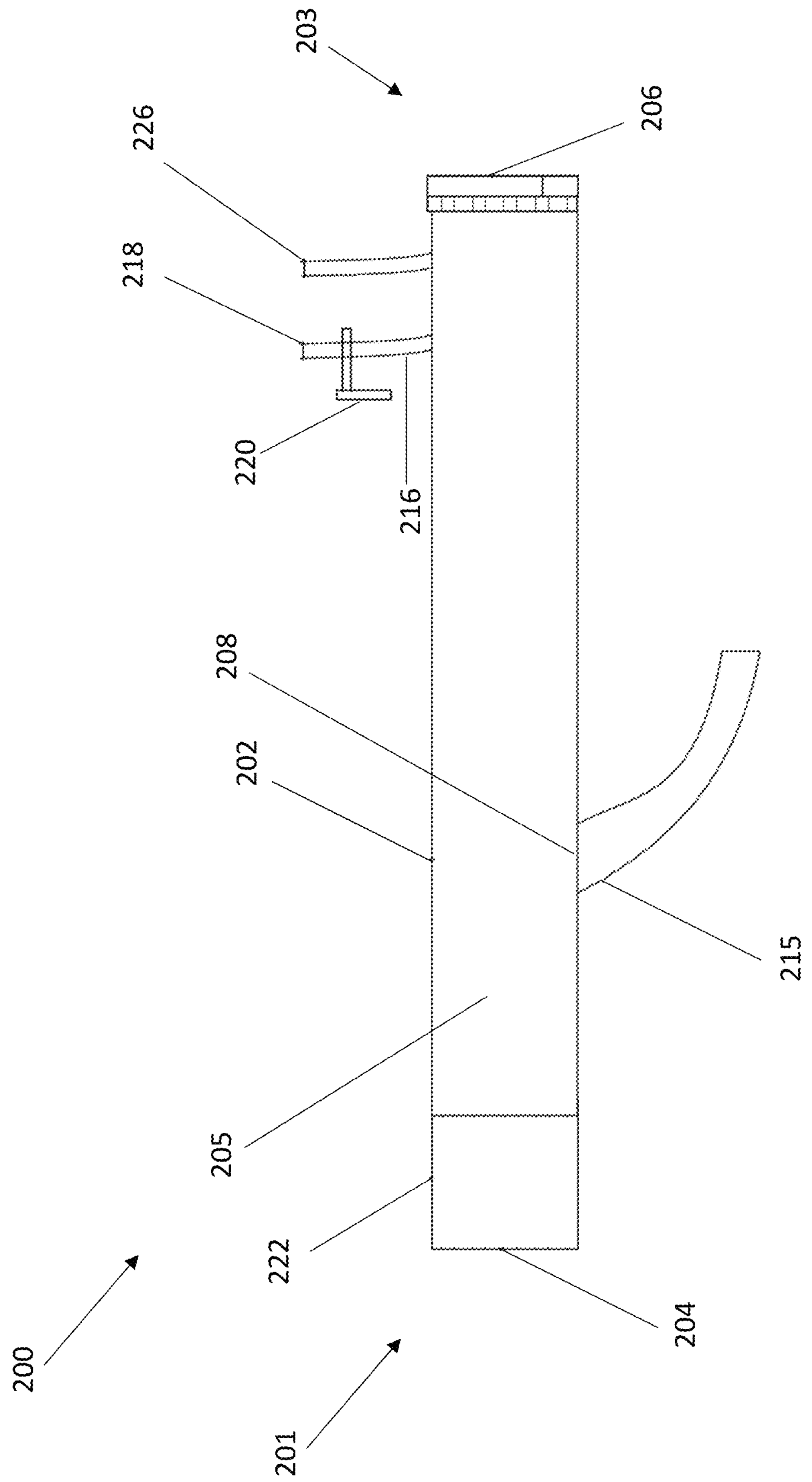
FIG. 2C depicts a side view of the dilators used to introduce an exemplary bi-directional sheath system.

Referring now to FIG. 2A through FIG. 2C, another exemplary bi-directional sheath system 200 of the present invention is shown. Bi-directional sheath system 200 comprises a proximal end 201, a distal end 203 and a sheath body 202 therebetween having an elongated cylindrical body comprising a sheath lumen 205. Sheath body 202 comprises a first opening 204 at proximal end 201, a second opening 206 at distal end 203, a third opening 208, an antegrade dilator 210, a retrograde dilator 212, a side lumen 215, and an end unit 222. Retrograde dilator 212 comprises at least one preformed curve (curved region) 214 towards proximal end 201.

Sheath body 202 may further comprise a side port 216 at distal end 203. Side port 216 is in fluid communication with sheath body 202. Side port 216 may be further connected to side port lumen 218 with three-way stopcock 220.

Sheath body 202, first opening 204, second opening 206, third opening 208, antegrade dilator 210, retrograde dilator 212, curved region 214, side lumen 215, side port 216, side port lumen 218, three-way stopcock 220 and end unit 222 function in the same manner as sheath body 102, first opening 104, second opening 106, third opening 108, antegrade dilator 110, retrograde dilator 112, curved region 114, side lumen 115, side port 116, side port lumen 118, three-way stopcock 120 and end unit 122 as explained somewhere else herein.

Sheath body 202, further comprises an inflation port 226 located near distal end 203. Inflation port 226 is in fluid communication with an intraluminal balloon assembly 224 mounted near proximal end 201 of antegrade dilator 210. Intraluminal balloon assembly 224 can be inflated through inflation lumen 228 and inflation port 226 to occlude proximal end 201 of sheath body 202, thereby providing fixture of antegrade dilator 210 in place, and thus favoring easier access to side lumen 215.

Intraluminal balloon assembly 224 may be made from any of a variety of materials known by those of skill in the art to be suitable for dilatation balloon manufacture. For example, intraluminal balloon assembly 224 may be formed of materials imparting relatively compliant expansion characteristics such as conventionally treated polyethylenes. When compliant materials are used, once fully inflated, the diameter of luminal balloon assembly 224 will tend to increase in response to further increases in inflation pressure, until a preset limit, at or below the burst pressure of intraluminal balloon assembly 224, is reached.

Alternatively, intraluminal balloon assembly 224 may be formed of materials imparting relatively noncompliant expansion characteristics such as conventional polyethylene terephthalate (PET) formulations. Balloons formed of noncompliant materials such as PET generally inflate to a predetermined inflation diameter, which is substantially maintained upon increasing inflation pressure, until a preset pressure, at or below the burst pressure of the balloon, is reached.

Figure 3A:
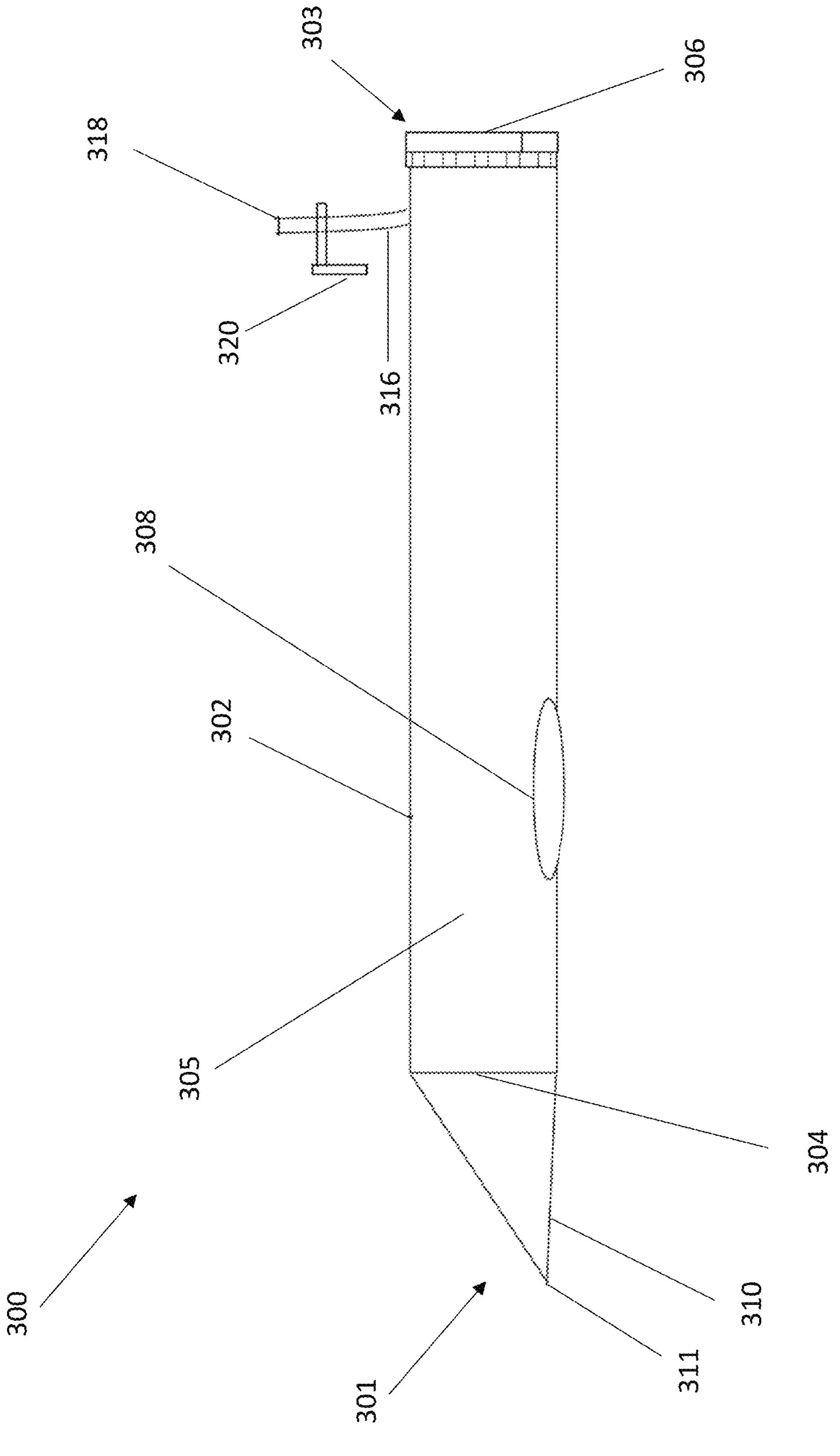
FIG. 3A depicts a side view of an exemplary bi-directional sheath system, after removal of the dilators.

Referring now to FIG. 3A, an exemplary bi-directional sheath system 300 of the present invention is shown. Bi-directional sheath system 300 comprises a proximal end 301, a distal end 303 and a sheath body 302 therebetween. Sheath body 302 has an elongated cylindrical body comprising a sheath lumen 305 with a diameter ranging between about 5-9 French. In one embodiment, sheath lumen 305 may have a diameter less than 5 French. In one embodiment, sheath lumen 305 may have a diameter more than 9 French. In one embodiment, sheath body 302 is approximately ranging between 5 cm-20 cm in length, however any suitable length may be used. Sheath body 302 comprises a first opening 304 at proximal end 301, a second opening 306 at distal end 303 and a third opening 308. In one embodiment, third opening 308 is located between first opening 304 and second opening 306 at any suitable distance away from first opening 304 and second opening 306. In one embodiment, the distance between first opening 304 and third opening 308 is more than the distance between the second opening 306 and the third opening 308. In one embodiment, the distance between first opening 304 and third opening 308 is less than the distance between the second opening 306 and the third opening 308. In one embodiment, first opening 304 and second opening 306 have a diameter ranging between 1.9-3.3 mm. In one embodiment, third opening 308 has a diameter ranging between 1.9-3.3 mm. In one embodiment, first opening 304, second opening 306 and third opening 308 may have a diameter less than 1.9 mm. In one embodiment, first opening 304, second opening 306 and third opening 308 may have a diameter more than 3.3 mm. In one embodiment, third opening 308 may include a radiopaque marker to aid a user in the placement and positioning of sheath body 302. In one embodiment, first opening 308 may include a radiopaque marker to aid a user in the placement and positioning of sheath body 302.

Second opening 306 provides access to the sheath lumen 305 for introduction of catheters, balloons and stent technology to complete the intended imaging or treatment.

Sheath body 302 may further comprise a side port 316 at distal end 303. Side port 316 is in fluid communication with sheath body 302. Side port 316 may be further connected to side port lumen 318 with three-way stopcock 320. Side port lumen 318 with three-way stopcock 320 allows for controlled release of fluids (e.g., saline, medicine, etc.) into sheath body 302.

In one embodiment, sheath body 302 may be constructed from a flexible polymer material or kink-resistant metal braid including but not limited to stainless steel or cobalt chromium. In one embodiment, sheath body may be made from a polymeric material, such as silicone, nylon, or urethane. Any medically acceptable thermoplastic or thermoset material may be used, including PTFE, a fluoropolymer, polyethylene, polypropylene, acetal, urethane, and others, however, it may be constructed from any material suitable for use within a blood vessel. In one embodiment, sheath body 302 may be made from a flexible material so that it is bendable throughout the length of sheath body 302 and at least at first opening 304, second opening 306 and third opening 308.

Figure 3B:
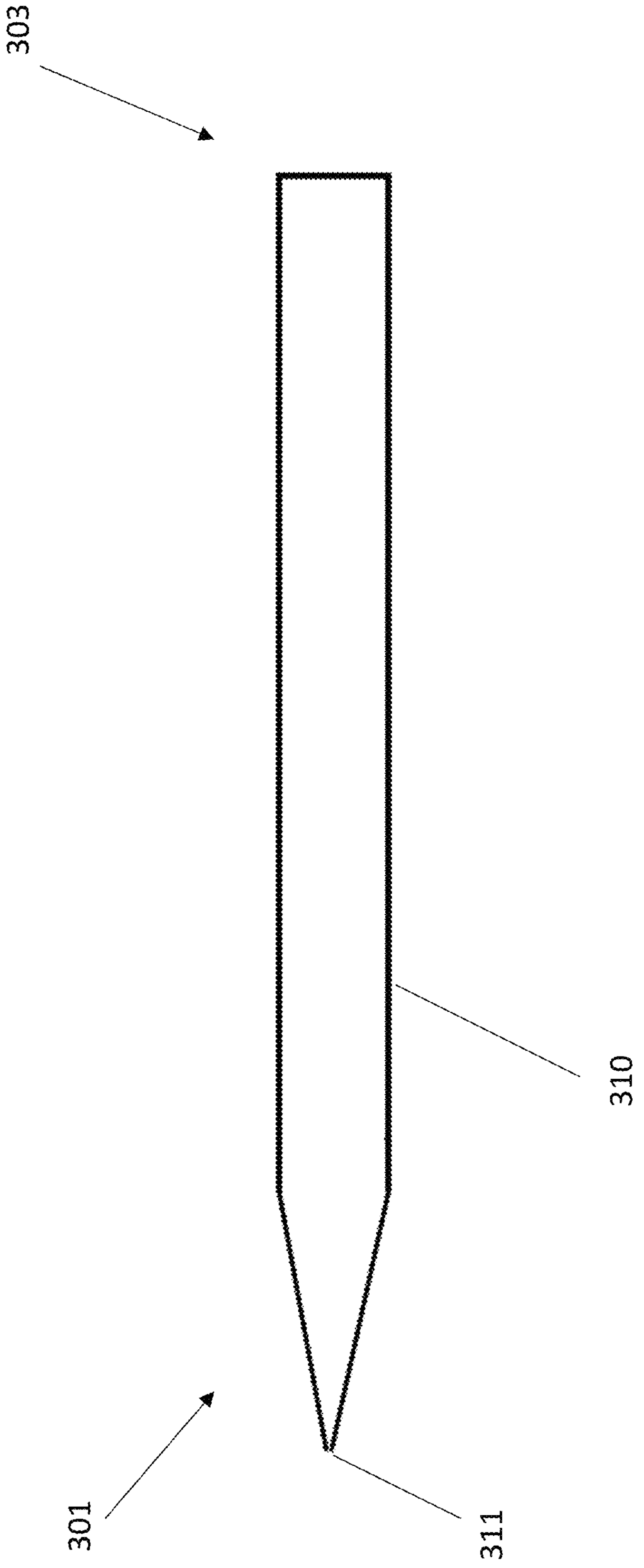
FIG. 3B depicts a side view of an exemplary bi-directional sheath system.

Referring now to FIG. 3B, sheath body 302 comprises an antegrade dilator 310 extending between second opening 306 and passes over first opening 304. This one-prong dilator system is intended for providing support and rigidity to the sheath system during introduction into the blood vessel. Antegrade dilator 310 is positioned in place through sheath lumen 305. Antegrade dilator 310 comprises a lumen connecting first opening 304 to second opening 306. In one embodiment, the lumen may be used for guide wire access. In one embodiment, antegrade dilator 310 has a diameter slightly less than the diameter of sheath body 302 to slide freely into sheath lumen 305. In one embodiment, antegrade dilator 310 is tapered at proximal end 301 for easier insertion. Antegrade dilator 310 further comprises an opening 311 at the end of proximal end 301. In one embodiment, the diameter of opening 311 ranges from 0.5 mm-1.2 mm. In one embodiment, first opening 304 is constructed so that it becomes occluded when antegrade dilator 310 is placed into the sheath and through first opening 304.

In one embodiment, antegrade dilator 310 may further include a radiopaque marker, which in one example is a circular marker band disposed around the tip of antegrade dilator 310. The marker band can include platinum, tantalum, palladium, gold, or any similar dense metal element, alloy, or compound that is visualized by imaging techniques.

Figure 3C:
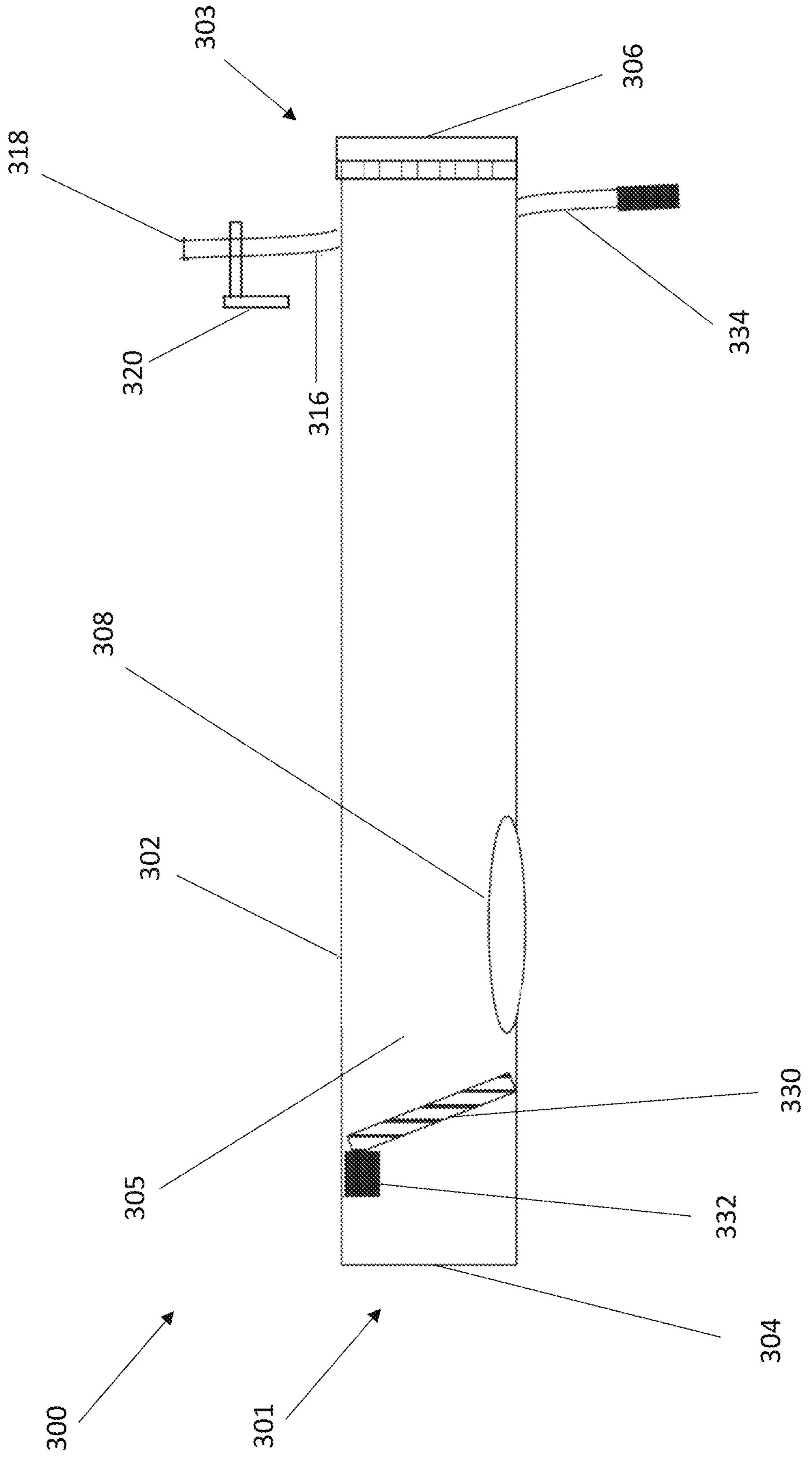
FIG. 3C depicts a side view detailing the common lumen and dual-dilator system of an exemplary bi-directional sheath system.
Figure 3D:
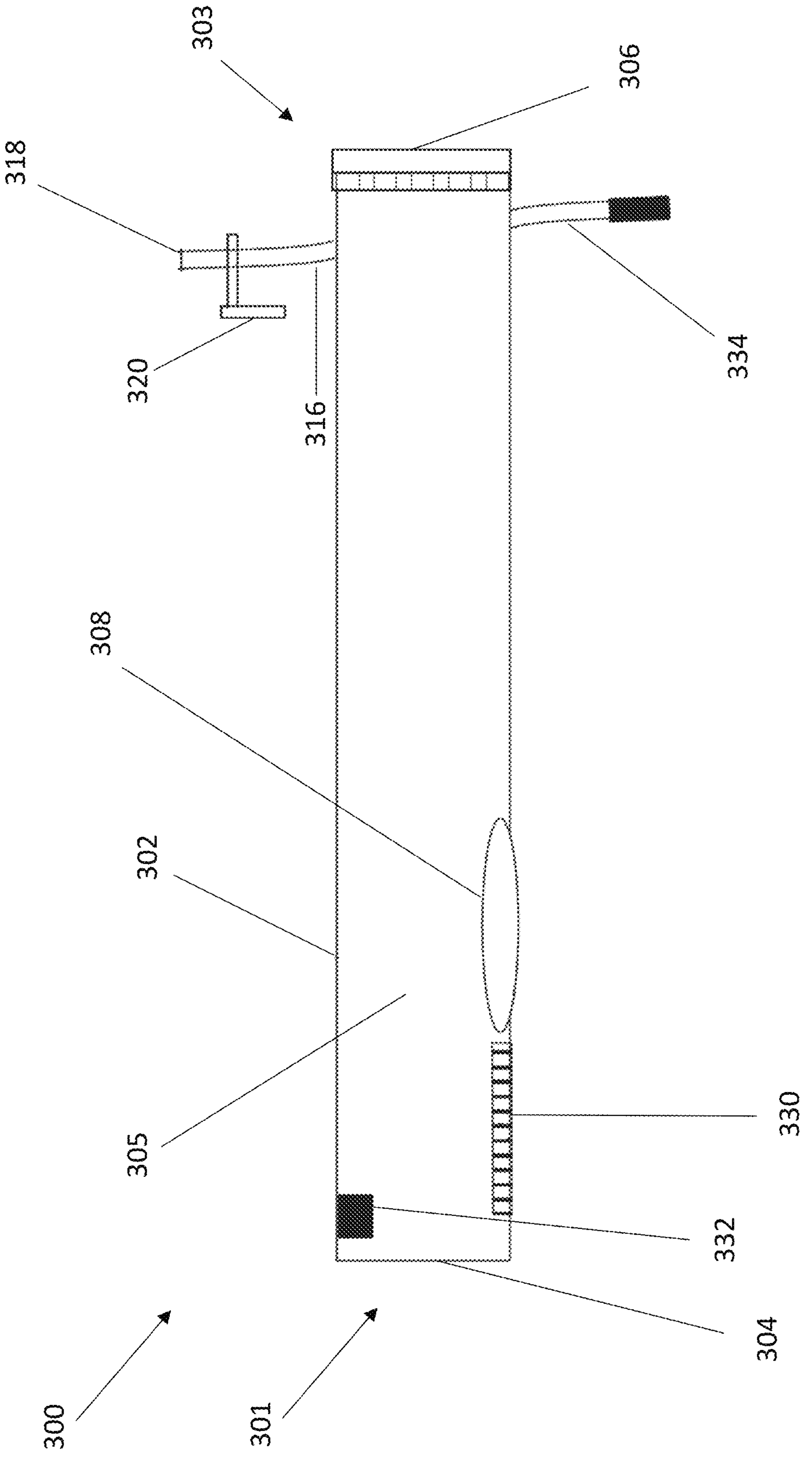
FIG. 3D depicts a side view detailing the common lumen and dual-dilator system of an exemplary bi-directional sheath system.

Referring now to FIG. 3C and FIG. 3D, sheath body 302 further comprises a trapdoor assembly comprising an intraluminal trapdoor 330, a crevice 332 and a deployment assembly 334. Trapdoor assembly allows single access to either first opening (antegrade access) 304 or third opening (retrograde access) 308 by blocking access to one, when access to the other one is desired.

Intraluminal trapdoor 330 is hingedly secured to sheath body 302 and extend radially within sheath lumen 305 to block access to first opening 304 (FIG. 3C). Intraluminal trapdoor 330 when deployed, occludes the antegrade lumen, allowing access to third opening 308 (retrograde access).

Deployment assembly 334 is configured to easily and quickly actuate crevice 332 to move laterally, thereby releasing trapdoor 330 into a retracted position, allowing access through first opening 304 (FIG. 3D). In such case, trapdoor 330 is permitted to open, thereby allowing passage of objects such as stents, catheters, balloons or alike through first opening.

In another embodiment, deployment assembly 334 is configured to easily and quickly actuate intraluminal trapdoor 330 to move between open and closed configuration. In one embodiment intraluminal trapdoor 330 is hinged and supported by a pin, which is in turn connected to a pin puller motor. When deployed, pin puller is actuated to retract pin. In one embodiment, any other mechanism known to one skilled in the art that can incorporate this motion and maneuverability of the trapdoor may be used. In such cases, intraluminal trapdoor 330 is open, thereby allowing passage of objects such as stents, catheters, balloons or alike through first opening.

This configuration permits introduction of guidewires, balloon and stent-devices in a bi-directional orientation. In one embodiment, simultaneous antegrade and retrograde access is not afforded with this exemplary bi-directional sheath system 300.

Any other suitable mechanism known to one skilled in the art may be used to transition between access to first opening and third opening.

Referring now to FIG. 4A through FIG. 4D, an exemplary bi-directional sheath system 400 of the present invention is shown. Bi-directional sheath system 400 comprises a proximal end 401, a distal end 403 and a sheath body 402 therebetween. Sheath body 402 has an elongated cylindrical body comprising a sheath lumen 405 with a diameter ranging between about 5-9 French. In one embodiment, sheath lumen 405 may have a diameter less than 5 French. In one embodiment, sheath lumen 405 may have a diameter more than 9 French. In one embodiment, sheath body 402 is approximately ranging between 5 cm-20 cm in length, however any suitable length may be used. Sheath body 402 comprises a first opening 404 at proximal end 401, a second opening 406 at distal end 403 and a third opening 408. In one embodiment, third opening 408 is located between first opening 404 and second opening 406 at any suitable distance away from first opening 404 and second opening 406. In one embodiment, the distance between first opening 404 and third opening 408 is more than the distance between the second opening 406 and the third opening 408. In one embodiment, the distance between first opening 404 and third opening 408 is less than the distance between the second opening 406 and the third opening 408. In one embodiment, first opening 404 and second opening 406 have a diameter ranging between 1.9-3.3 mm. In one embodiment, third opening 408 has a diameter ranging between 1.9-3.3 mm. In one embodiment, first opening 404, second opening 406 and third opening 408 may have a diameter less than 1.9 mm. In one embodiment, first opening 404, second opening 406 and third opening 408 may have a diameter more than 3.3 mm. In one embodiment, third opening 408 may include a radiopaque marker to aid a user in the placement and positioning of sheath body 402. In one embodiment, first opening 404 may include a radiopaque marker to aid a user in the placement and positioning of sheath body 402.

Second opening 406 provides access to the sheath lumen 405 for introduction of catheters, balloons, and stent technology to complete the intended imaging or treatment.

In one embodiment, sheath body 402 may be constructed from a flexible polymer material or kink-resistant metal braid including but not limited to stainless steel or cobalt chromium. In one embodiment, sheath body may be made from a polymeric material, such as silicone, nylon, or urethane. Any medically acceptable thermoplastic or thermoset material may be used, including PTFE, a fluoropolymer, polyethylene, polypropylene, acetal, urethane, and others, however, it may be constructed from any material suitable for use within a blood vessel. In one embodiment, sheath body 402 may be made from a flexible material so that it is bendable throughout the length of sheath body 402 and at least at first opening 404, second opening 406 and third opening 408.

Sheath body 402 comprises an antegrade dilator 410 and a retrograde dilator 412. This two-pronged dilator system (comprising antegrade dilator 410 and a retrograde dilator 412) is intended for providing support and rigidity to the sheath system during introduction into the blood vessel. Antegrade dilator 410 and retrograde dilator 412 are positioned in place through sheath lumen 405. In one embodiment, antegrade dilator 410 and retrograde dilator 412 are removable. Antegrade dilator 410 comprises a lumen connecting first opening 404 to second opening 406. In one embodiment, the lumen may be used for guide wire access. In one embodiment, antegrade dilator 410 has a diameter ranging from 5-9 French at first opening 404. In one embodiment, antegrade dilator 410 has a diameter ranging from approximately 1.2 mm-3 mm at second opening 406. In one embodiment, antegrade dilator 410 is tapered at proximal end 401 for easier insertion. Antegrade dilator 410 further comprises an opening 411 at the end of proximal end 401. In one embodiment, the diameter of opening 411 ranges from 0.5 mm-1.2 mm. In one embodiment, first opening 404 is constructed so that it becomes occluded when antegrade dilator 410 is placed into the sheath and through first opening 404. In one embodiment, second opening 406 is of a bi-luminal construction such that it includes a antegrade dilator 410 and retrograde dilator 412. In one embodiment, antegrade dilator 410 and retrograde dilator 412 have the same diameter at second opening 406. In one embodiment, antegrade dilator 410 has a diameter larger than retrograde dilator 412 at second opening 406. In one embodiment, antegrade dilator 410 has a diameter smaller than retrograde dilator 412 at second opening 406. In one embodiment, antegrade dilator 410 is oriented towards the heart/head. In one embodiment, antegrade dilator 410 may be oriented towards the periphery/extremities.

Antegrade dilator 410 shares sheath lumen 405 with retrograde dilator 412 from second opening 406 to third opening 408. In one embodiment, after this point antegrade dilator 410 has a larger diameter to fit sheath lumen 405 and occlude first opening 404. In one embodiment, antegrade dilator 410 has a constant diameter throughout sheath lumen 405, from second opening 406 to first opening 404.

In one embodiment, antegrade dilator 410 may further include a radiopaque marker, which in one example is a circular marker band disposed around the tip of antegrade dilator 410. The marker band can include platinum, tantalum, palladium, gold, or any similar dense metal element, alloy, or compound that is visualized by imaging techniques.

Retrograde dilator 412 connects second opening 406 to third opening 408. Retrograde dilator 412 comprises a lumen for guide wire access. In one embodiment, retrograde dilator 412 has a diameter ranging from approximately 1 mm-2 mm. In some embodiments, retrograde dilator 412 comprises at least one preformed curve (curved region) 414 at proximal end 401. Curved region 414 can have any curved configuration, including but not limited to loops, bends, hooks, spirals, twists, pigtail curves, Judkins style curves, Amplatz style curves, SOS style curves, cobra style curves, Simmons style curves, Bernstein style curves, and the like in a primary curve, secondary curve, tertiary curve, or more. Curved region 414 may be pre-formed, such as by heat setting. In one embodiment, retrograde dilator 412 may include portions or regions having the desired stiffness, rigidity and flexibility necessary for proper insertion into the subject and subsequent functionality. In some embodiments, curved region 414 is at least partially flexible, such that curved region 414 may be temporarily straightened using a stylet, or such that the at least one preformed curve may be advanced over a guidewire. In some embodiments, retrograde dilator 412 further comprises an opening 413 at distal end 403. In one embodiment, the diameter of opening 413 ranges from 0.5 mm-1.2 mm. In one embodiment, retrograde dilator 412 is oriented towards the feet, if antegrade dilator 410 is oriented towards the head. In one embodiment, retrograde dilator 412 is oriented towards the head, if antegrade dilator 410 is oriented towards the feet.

In one embodiment, antegrade dilator 410 and retrograde dilator 412 are each made of a flexible polymer. Some examples of suitable polymers may include, but are not limited to, polytetrafluoroethylene (PTFE), ethylene tetrafluoroethylene (ETFE), fluorinated ethylene propylene (FEP), polyoxymethylene (POM, for example, DELRIN® available from DuPont), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plasties), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In one embodiment, antegrade dilator 410 and retrograde dilator 412 may be made of soft polymer material to facilitate movement through the patient's blood vessels. The soft polymer is less rigid and more malleable than the hard polymer and less likely to bounce or move suddenly when contacts the vessel wall.

Figure 4A:
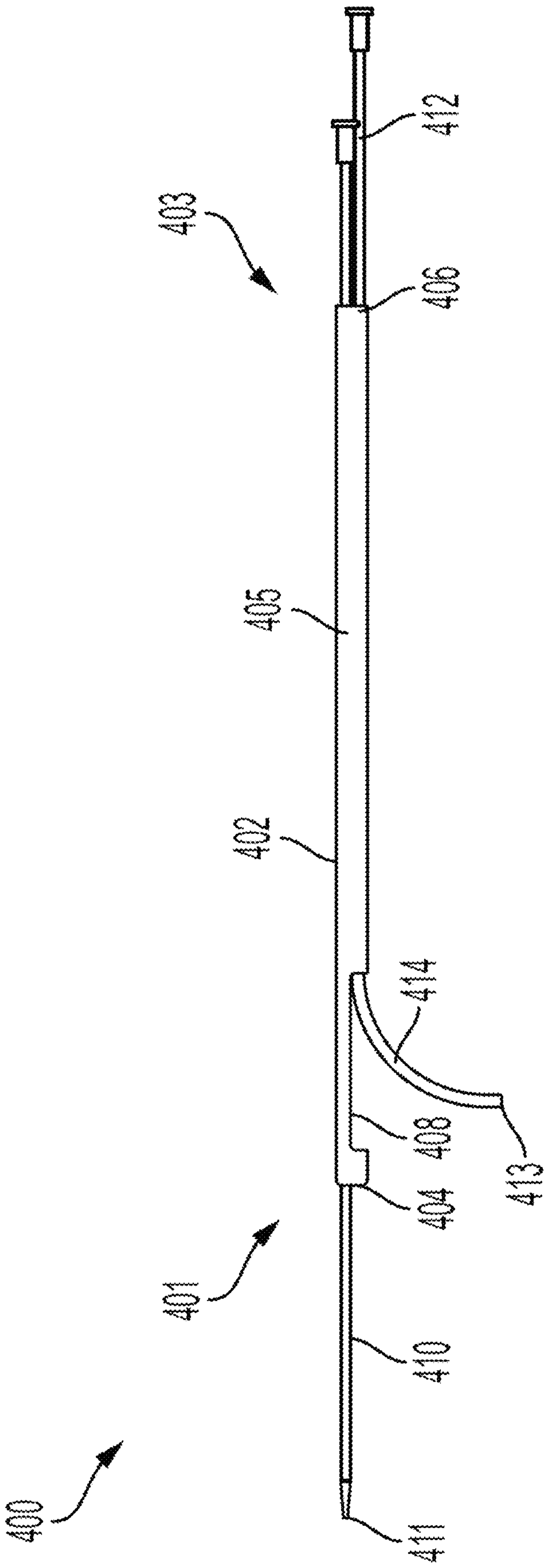
FIG. 4A depicts a side view of an exemplary bi-directional sheath system with antegrade dilator in place and the retrograde limb deployed.
Figure 4B:
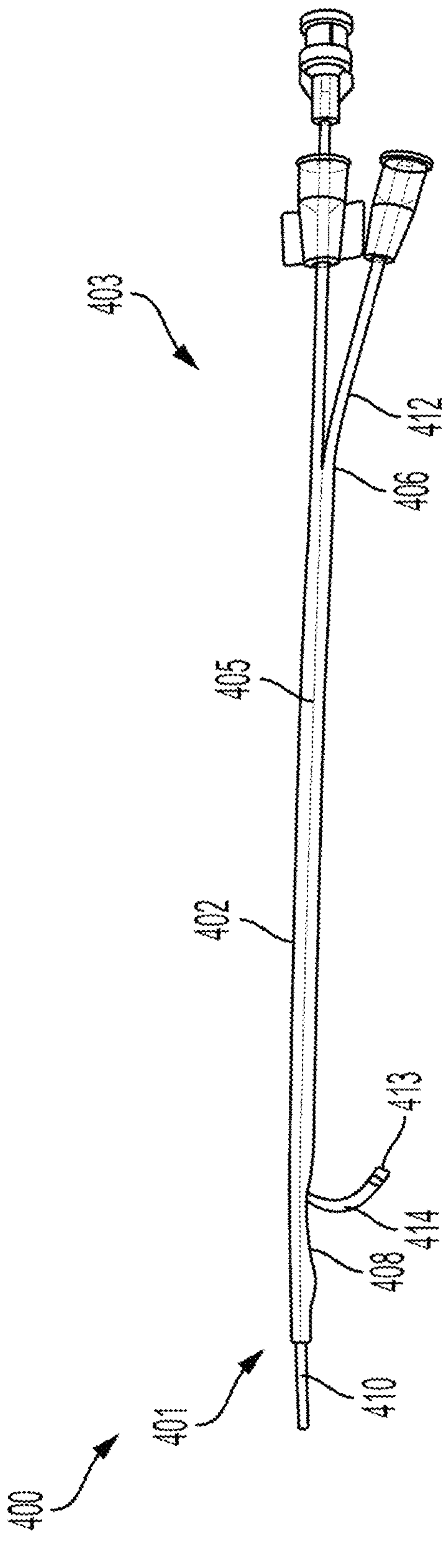
FIG. 4B depicts a side view of an exemplary bi-directional sheath system with a fixed retrograde limb.
Figure 4B:
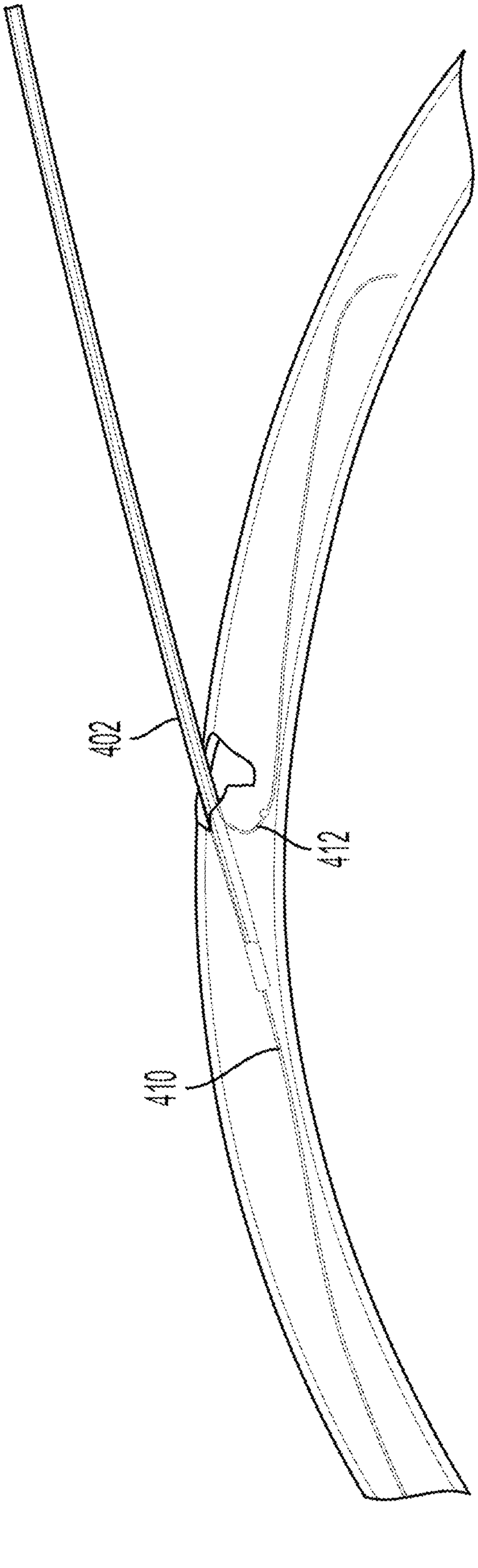
Figure 4C:
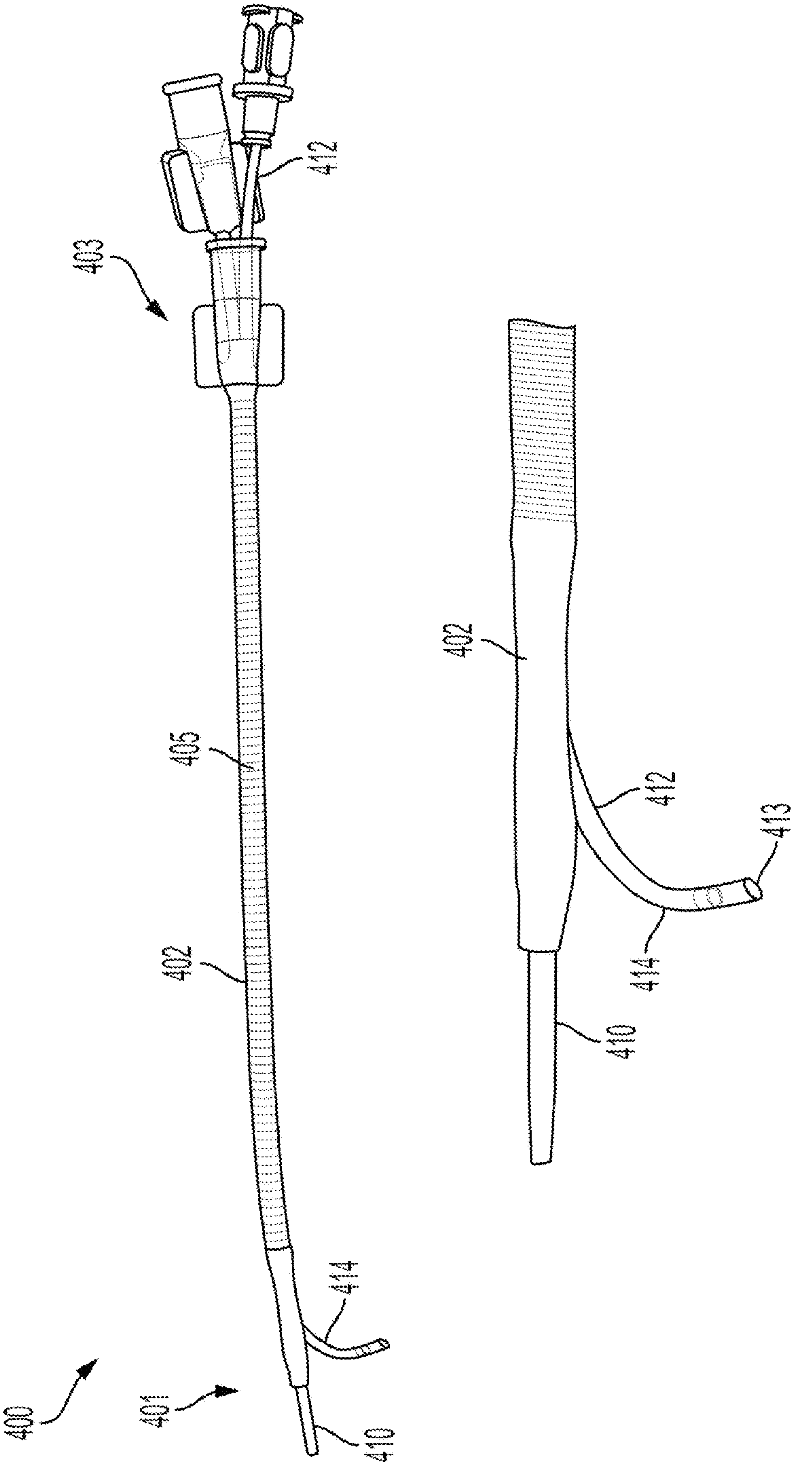
FIG. 4C depicts a side view of an exemplary bi-directional sheath system with a movable retrograde limb.
Figure 4D:
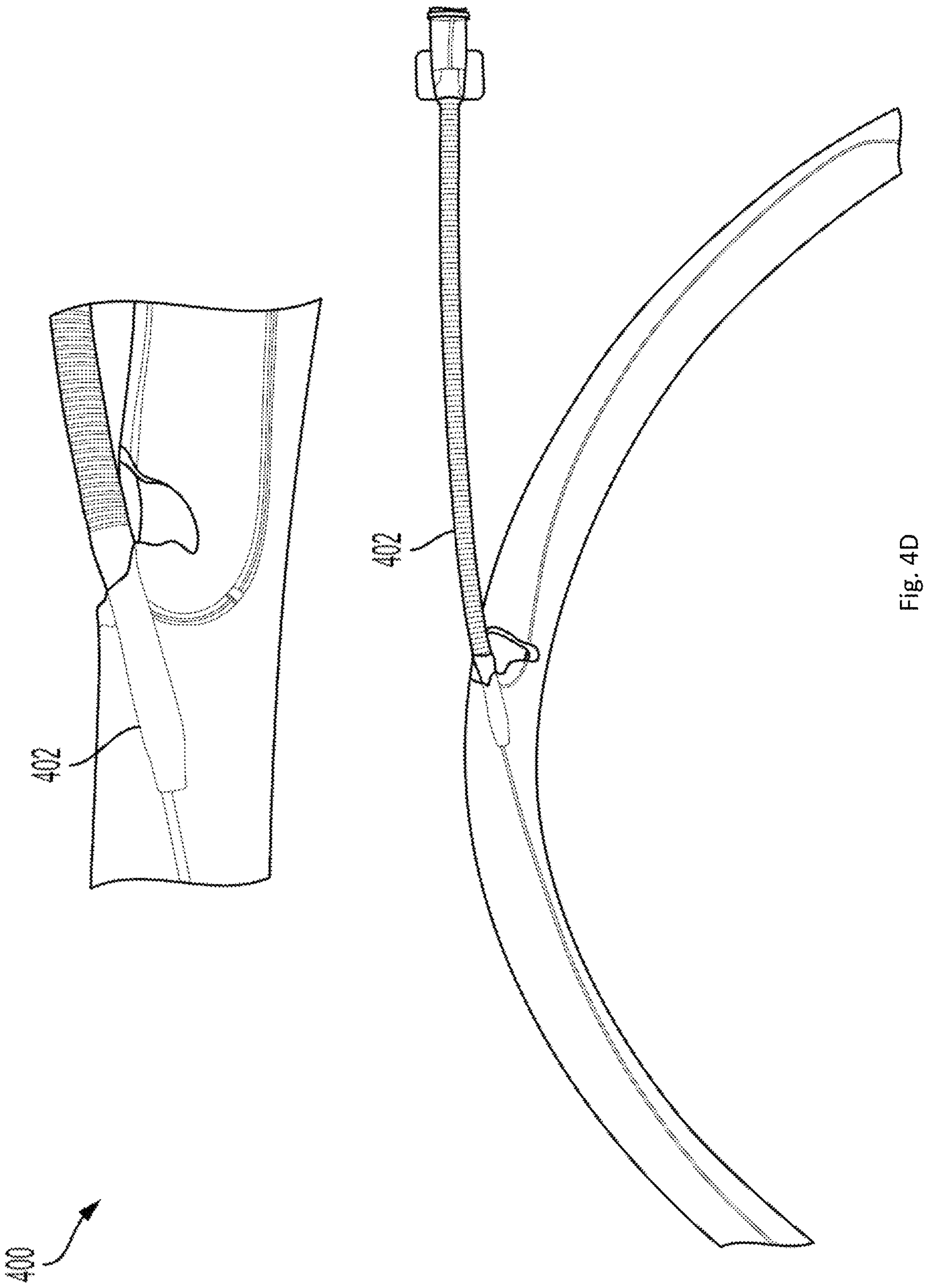
FIG. 4D depicts a close-up view of an exemplary bi-directional sheath system with the antegrade dilator and a moveable retrograde limb.

In one embodiment, retrograde dilator 412 may be fixed in place (FIG. 4B). In one embodiment, device with a fixed retrograde dilator 412 in place, may be used in diagnostic applications. In one embodiment, one of the dilators may be fixed in place, while the other one is mobile. In one embodiment, retrograde dilator 412 may be mobile along the length of third opening 408. In one embodiment, retrograde dilator 412 may be mobile along the length of sheath lumen 405. In one embodiment, antegrade dilator 410 and retrograde dilator 412 may both be mobile (FIG. 4C and FIG. 4D). In one embodiment, device having two mobile dilators may be used in diagnostic and therapeutic application.

Method of Use

The present invention also relates to methods for using the bi-directional sheath system described above to provide bi-directional vascular access. The methods described herein have the potential to enable endovascular imaging and treatment of concomitant multiple lesions, both in antegrade and retrograde direction. Further, the methods described herein have the potential to transform modes of endovascular imaging and treatment of blood vessels, relating to the fields of cardiology, radiology, cardiothoracic surgery, pulmonology, nephrology, neurology, neurosurgery and vascular surgery. In one embodiment, the method of present invention may reduce the number of procedures performed for endovascular imaging and treatment of multiple concomitant lesions in blood vessels. In one embodiment, this method may reduce the number of blood vessel access sites for endovascular imaging and treatment of multiple concomitant lesions, thus dramatically reducing the rate of complications from access.

Figure 5:
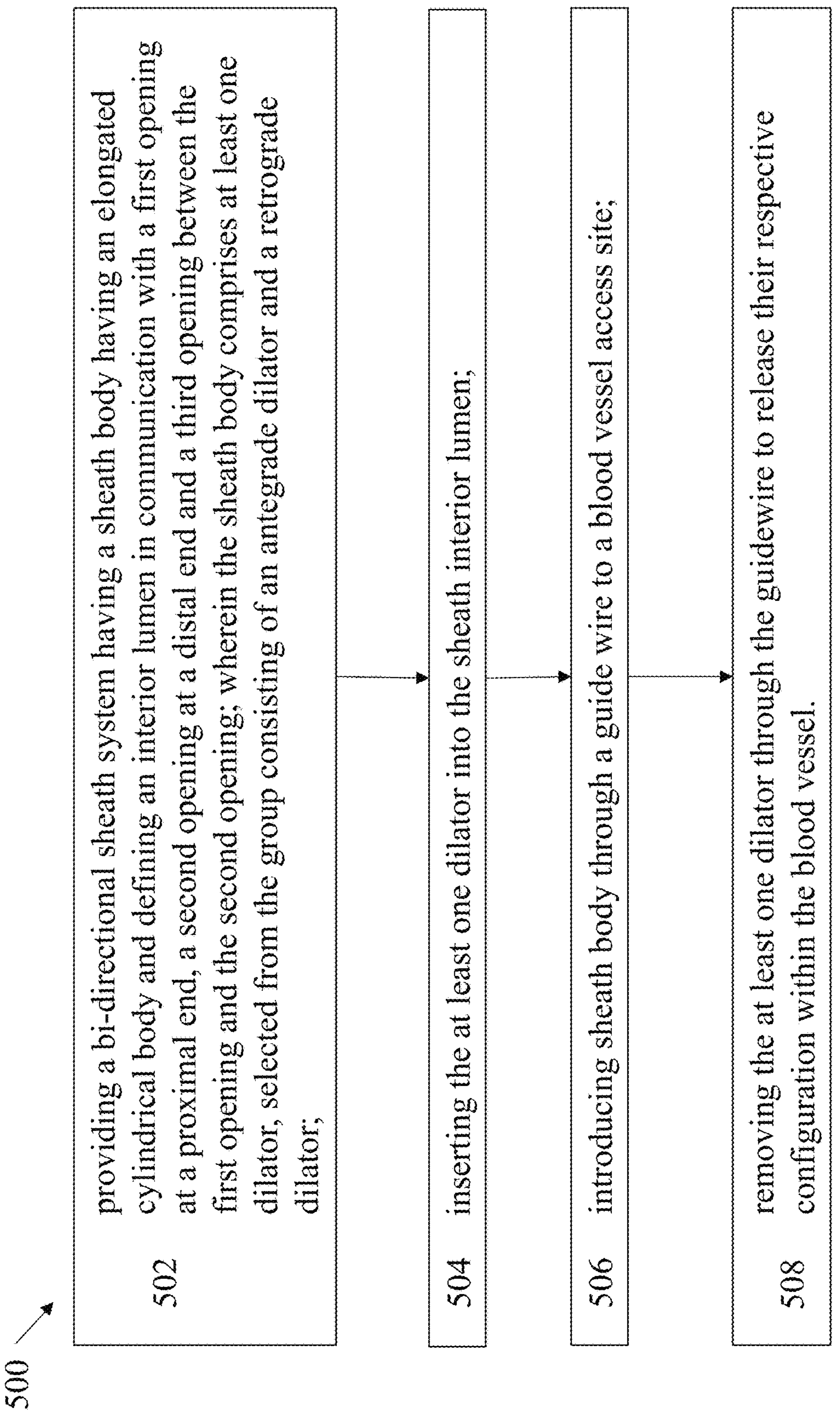
FIG. 5 is a flowchart depicting an exemplary method of accessing concomitant multiple lesions for endovascular imaging and treatment.

Referring now to FIG. 5, an exemplary method 500 of using the bi-directional sheath system of the present invention is depicted. Method 500 begins with step 502, wherein a bi-directional sheath system is provided, the bi-directional sheath system comprising a sheath body having an elongated cylindrical body and defining an interior lumen in communication with a first opening at a proximal end, a second opening at a distal end and a third opening between the first opening and the second opening; wherein the sheath body comprises at least one dilator, selected from the group consisting of an antegrade dilator and a retrograde dilator. The antegrade dilator comprises a lumen connecting the first opening to second opening, and the retrograde dilator comprises a lumen connecting the second opening to the third opening. In step 504, at least one dilator is inserted into the sheath interior lumen. In step 506, sheath body is introduced through a guide wire to a blood vessel access site. In step 508, the at least one dilator is removed through the guidewire to release the sheath body's respective configuration within the blood vessel.

In one embodiment, sheath body comprises an intraluminal trapdoor and a deployment assembly, wherein the intraluminal trapdoor is hingedly secured to sheath body and extend radially within sheath lumen to block access to first opening when deployed. In this configuration, the method comprises a further step of actuating a crevice to move laterally, thereby releasing the intraluminal trapdoor into a retracted position, allowing access through the first opening.

In one embodiment, sheath body further comprises an intraluminal balloon assembly in fluid connection with an inflation port located near the distal end through an inflation lumen located therebetween. In this configuration, the method comprises a further step of inflating the luminal balloon assembly through the inflation lumen and the inflation port to occlude proximal end of sheath body, thereby providing fixture of the antegrade dilator in place.

The disclosures of each and every patent, patent application, and publication cited herein are hereby each incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A bi-directional sheath system comprising:

a sheath body having an elongated cylindrical body and defining an interior lumen in communication with a first opening at the proximal end and second opening at the distal end and a third opening located between the first opening and the second opening of the sheath body;

wherein the sheath body comprises an antegrade dilator and a retrograde dilator, wherein the antegrade dilator comprises a lumen connecting the first opening to second opening, and the retrograde dilator comprises a lumen connecting the second opening to the third opening;

wherein the antegrade dilator and the retrograde dilator are removable from the sheath body;

wherein the sheath body further comprises a side port at the distal end, wherein the side port is in fluid communication with the sheath body.

2. The bi-directional sheath system of claim 1, wherein the distance between the first opening and the third opening is less than the distance between the second opening and the third opening.

3. The bi-directional sheath system of claim 1, wherein the retrograde dilator comprises at least one preformed curve at proximal end, wherein the at least one preformed curve is at least partially flexible.

4. The bi-directional sheath system of claim 1, wherein the sheath body further comprises a side lumen fluidly connected to the sheath body through the third opening.

5. The bi-directional sheath system of claim 4, wherein the side lumen has an angle ranging between 25°-75° with respect to the sheath body.

6. The bi-directional sheath system of claim 1, wherein the side port is further connected to a side port lumen with a three-way stopcock, wherein the side port lumen and the three-way stopcock allow for controlled release of fluids selected from the group consisting of saline and medicine into the sheath body.

7. The bi-directional sheath system of claim 1, wherein the sheath body further comprises an intraluminal balloon assembly in fluid connection with an inflation port located near the distal end through an inflation lumen located therebetween, wherein the luminal balloon assembly can be inflated through the inflation lumen and the inflation port to occlude proximal end of sheath body, thereby providing fixture of the antegrade dilator in place.

8. The bi-directional sheath system of claim 1, wherein the sheath body further comprises an intraluminal trapdoor and a deployment assembly, wherein the intraluminal trapdoor is hingedly secured to sheath body and extend radially within sheath lumen to block access to first opening when deployed.

9. The bi-directional sheath system of claim 8, wherein the deployment assembly is configured to actuate a crevice to move laterally, thereby releasing the intraluminal trapdoor into a retracted position, allowing access through the first opening.

10. A method of using a bi-directional sheath system comprising:

providing a bi-directional sheath system having a sheath body having an elongated cylindrical body and defining an interior lumen in communication with a first opening at a proximal end, a second opening at a distal end and a third opening between the first opening and the second opening; wherein the sheath body comprises an antegrade dilator and a retrograde dilator, wherein the antegrade dilator and the retrograde dilator are removable from the sheath body, wherein the sheath body further comprises a side port at the distal end, wherein the side port is in fluid communication with the sheath body;

inserting the antegrade dilator and the retrograde dilator into the sheath interior lumen;

introducing the sheath body using a guide wire to a blood vessel access site;

removing the antegrade dilator and the retrograde dilator over the guidewire to release the sheath body's respective configuration within the blood vessel.

11. The method of claim 10, wherein the distance between the first opening and the third opening is less than the distance between the second opening and the third opening.

12. The method of claim 10, wherein the retrograde dilator comprises at least one preformed curve (curved region) at proximal end, wherein the curved region is at least partially flexible, such that the curved region may be temporarily straightened using a stylet.

13. The method of claim 10, wherein sheath body further comprises a side lumen fluidly connected to sheath body through the third opening.

14. The method of claim 10, wherein the side lumen has an angle ranging between 25°-75° with respect to the sheath body.

15. The method of claim 10, wherein the side port is further connected to a side port lumen with a three-way stopcock, wherein the side port lumen and the three-way stopcock allow for controlled release of fluids selected from the group consisting of saline and medicine into the sheath body.

16. The method of claim 10, wherein the sheath body further comprises an intraluminal balloon assembly in fluid connection with an inflation port located near the distal end through an inflation lumen located therebetween, wherein the luminal balloon assembly can be inflated through the inflation lumen and the inflation port to occlude proximal end of sheath body, thereby providing fixture of the antegrade dilator in place.

17. The method of claim 10, wherein the sheath body further comprises an intraluminal trapdoor, a crevice and a deployment assembly, wherein the intraluminal trapdoor is hingedly secured to sheath body and extends radially within the sheath lumen to block access to first opening when deployed.

18. The method of claim 17, wherein the deployment assembly is configured to actuate the crevice to move laterally, thereby releasing the intraluminal trapdoor into a retracted position, allowing access through the first opening.

* * * * *